United States Patent
Zhang et al.

(10) Patent No.: US 9,216,020 B2
(45) Date of Patent: Dec. 22, 2015

(54) ENDOSCOPIC SURGICAL CUTTING STAPLER WITH A CHAIN ARTICULATION

(75) Inventors: Zuren Zhang, Shanghai (CN); Yikang Jiang, Changzhou (CN); Zhenyu Jiang, Changzhou (CN); Rong Ji, Changzhou (CN); Yiyi Zhang, Shanghai (CN); Weihua Xu, Shanghai (CN); Dongkun Yuan, Changzhou (CN); Qi Yang, Changzhou (CN)

(73) Assignee: CHANGZHOU KANGDI MEDICAL STAPLER CO., LTD., Xinbei District, Changzhou, Jiangsu (CN)

( * ) Notice: Subject to any disclaimer, the term of this patent is extended or adjusted under 35 U.S.C. 154(b) by 503 days.

(21) Appl. No.: 13/812,839

(22) PCT Filed: Dec. 14, 2010

(86) PCT No.: PCT/CN2010/079787
§ 371 (c)(1),
(2), (4) Date: Jan. 28, 2013

(87) PCT Pub. No.: WO2012/040983
PCT Pub. Date: Apr. 5, 2012

(65) Prior Publication Data
US 2013/0126586 A1    May 23, 2013

(30) Foreign Application Priority Data
Sep. 30, 2010   (CN) .......................... 2010 1 0299416

(51) Int. Cl.
*A61B 17/068*   (2006.01)
*A61B 17/072*   (2006.01)
*A61B 17/00*    (2006.01)
*A61B 17/29*    (2006.01)

(52) U.S. Cl.
CPC .......... *A61B 17/068* (2013.01); *A61B 17/07207* (2013.01); *A61B 2017/00314* (2013.01); *A61B 2017/2908* (2013.01); *A61B 2017/2927* (2013.01)

(58) Field of Classification Search
CPC . A61B 17/068; A61B 17/072; A61B 17/1155
USPC .................... 227/175.1, 176.1, 179.1, 180.1; 606/153, 219
See application file for complete search history.

(56) References Cited

U.S. PATENT DOCUMENTS

| | | | |
|---|---|---|---|
| 7,087,071 B2 * | 8/2006 | Nicholas et al. | 606/206 |
| 7,954,685 B2 * | 6/2011 | Viola | 227/175.1 |
| 2007/0084899 A1 * | 4/2007 | Taylor | 227/176.1 |

* cited by examiner

*Primary Examiner* — Hemant M Desai
*Assistant Examiner* — Nathaniel Chukwurah
(74) *Attorney, Agent, or Firm* — Global IP Services; Tianhua Gu

(57) ABSTRACT

An endoscopic surgical cutting stapler with a chain articulation is provided, in which a joint is implemented by a chain articulation, teeth are provided at two ends of a chain plate of the chain articulation, and teeth of adjacent chain plates in the same row are engaged. Through mesh transmission of engaged teeth of the adjacent chain plates in the same row, an angle of a most proximal chain plate of the chain articulation is gradually multiplied at several stages and transmitted to an end effector. The end effector can rotate for 90° with small drive motion of the operating mechanism, thereby achieving precise placement of the chain articulation after rotation. The end effector can be precisely aligned with a part to be cut and stapled, and a radius of curvature of the chain articulation can be significantly increased.

11 Claims, 18 Drawing Sheets

ENDOSCOPIC SURGICAL CUTTING STAPLER WITH A CHAIN ARTICULATION

CROSS REFERENCE TO RELATED PATENT APPLICATION

The present application is the US national stage of PCT/CN2010/079787 filed on Dec. 14, 2010, which claims the priority of the Chinese patent application No. 201010299416.X filed on Sep. 30, 2010, which application is incorporated herein by reference.

BACKGROUND OF THE PRESENT INVENTION

1. Field of Invention

The present invention relates to an endoscopic surgical cutting stapler used in endoscopic surgeries, specifically to an endoscopic surgical cutting stapler used in laparoscopic surgeries and an endoscopic surgical cutting stapler used in thoracoscopic surgeries, and more specifically to an endoscopic surgical cutting stapler with a chain articulation.

2. Description of Related Arts

In laparoscopic surgeries and thoracoscopic surgeries, an endoscopic surgical cutting stapler is usually used in cutting and stapling surgeries on esophagus, stomach, duodenum, small intestine, colon, rectum, vermiform appendix, gallbladder, pancreas, and spleen in the digestive tract, in cutting and stapling surgeries on lung and trachea in the respiratory tract, and also in cutting and stapling surgeries on bladder and uterus in the genitourinary system, so as to shorten the surgery period and improve the surgery quality.

US Patent Publication No. US20080308602, No. US20090206124, and No. US20090206137 disclose various endoscopic surgical cutting staplers in the prior art. When an endoscopic surgical cutting stapler is used, an end effector first enters a body cavity through a puncture needle with an inner diameter of 12 mm to 13 mm. Then the end effector is controlled to perform axial rotation and joint rotation, so as to be aligned with tissue to be cut and stapled. At this time, a clamping mechanism can be operated, and a slide bar is pushed, to clamp the tissue to be cut and stapled between a staple anvil and a staple cartridge of the end effector. An actuation mechanism is then operated, and the slide bar is further pushed. Two ends of the slide bar are respectively inserted into the staple anvil and staple cartridge of the end effector, so that a required clamping thickness is achieved between the staple anvil and staple cartridge. The slide bar pushes the staple pushing block through a staple pushing sled, to eject the staple from the staple cartridge through the clamped tissue to be cut and stapled and against a staple forming slot on the staple anvil, so that the U-shaped staple is deformed into a B-shaped staple, thereby stapling the tissue. A cutter blade on the slide bar cuts the clamped tissue to be cut and stapled, so as to achieve the surgery purpose of cutting the tissue. After the cutting and stapling operations, the clamping mechanism is operated to loosen the cut and stapled tissue, so that the tissue exits the endoscopic surgical cutting stapler. Other operating mechanisms may also be used as the clamping mechanism and the actuation mechanism of the endoscopic surgical cutting stapler. The operating mechanism may further include an indicating mechanism. Operating mechanisms such as the clamping mechanism and the actuation mechanism of the endoscopic surgical cutting stapler may be manual endoscopic surgical cutting staplers disclosed in US Patent Publication No. US20080308602 and No. US20090206137, electric endoscopic surgical cutting staplers disclosed in US Patent Publication No. US20090090763 and No. US20090095790, or fluid-driven endoscopic surgical cutting stapler disclosed in US Patent Publication No. US20070125826 and No. US20080029577.

An existing endoscopic surgical cutting stapler includes an end effector, an articulation, an extension tube, a stapler body, and an operating mechanism. The operating mechanism is located on the stapler body, and is used to control an action of the end effector. The end effector, the articulation, the extension tube, and the stapler body are connected in sequence. The end effector consists of a support, a slide bar, a staple cartridge, and a staple anvil. The slide bar, the staple cartridge, and the staple anvil are mounted on the support. The staple cartridge consists of a staple cartridge housing, staple pushing blocks, a staple pushing sled, and staples. Staple slots, staple pushing holes, sled slots, and a blade pushing slot are provided in the staple cartridge housing. The staples are mounted in the staple slots. The staple pushing blocks are mounted in the staple pushing holes. The staple pushing sled is mounted in the blade pushing slot and the sled slot. The staple slots and the staple pushing holes of the staple cartridge housing are aligned in rows at two sides of the blade pushing slot. The staple pushing block is movable in the staple pushing hole to force the staple out of the staple slot. The staple pushing sled pushes the staple pushing block to move in the staple pushing hole through a slope, thereby forcing the staple out of the staple slot. The staple is U-shaped and consists of two staple legs, a staple beam, and two staple tips. One end of each staple leg is connected to the staple beam, and the other end is the staple tip. The staple may be made of stainless steel wires, tantalum wires, titanium wires, or other metal wires having similar properties. Two staple legs are inserted in the staple slot. The staple beam is seated at an upper edge of the staple pushing block. An end surface of the staple anvil is provided with staple forming slots corresponding to positions of the staples in the staple cartridge, and is also provided with a cutting slot corresponding to a position of the blade pushing slot in the staple cartridge housing. The staple forming slots of the staple anvil are correspondingly aligned in rows at two sides of the cutting slot of the staple anvil. The staple slots and staple pushing holes of the staple cartridge, and the staple forming slots of the staple anvil may be aligned in two rows, three rows, four rows, five rows, six rows, seven rows, or eight rows according to the cutting and stapling requirements of surgeries. The staple anvil may be pivoted to the support. The slide bar is movable in the blade pushing slot of the staple cartridge and the cutting slot of the staple anvil. When the staple anvil pivotally rotates around the support, the staple anvil and the staple cartridge clamp or loosen the tissue to be cut and stapled. When a required gap is achieved between the staple anvil and the staple cartridge, a required clamping thickness of the tissue to be cut and stapled is achieved between the staple anvil and the staple cartridge.

When the endoscopic surgical cutting stapler is used, an end effector first enters a body cavity through a puncture needle with an inner diameter of 12 mm to 13 mm. Then the end effector is controlled to perform axial rotation and joint rotation, so as to be aligned with the tissue to be cut and stapled. If the end effector fails to be aligned with the tissue to be cut and stapled, the end effector cannot clamp the tissue to be cut and stapled between the staple anvil and staple cartridge, and cannot perform cutting and stapling operations. In endoscopic surgical cutting staplers disclosed in US Patent Publication No. US20090206131 and No. 20100163597, the end effector and the extension tube are jointed through a pivot pin. The slide bar is formed by stacked thin plates. The end effector is pulled by a pull rod extending from the extension tube and sleeved on the end effector, thereby controlling the end effector to perform joint rotation around the pivot pin and relative to the extension tube. The thin plates of the slide bar rotate toward two sides along with the articulation and are bended toward the two sides. Such endoscopic surgical cutting stapler has the following disadvantage: restricted by the pivot pin, the end effector can only perform joint rotation around the pivot pin and relative to the extension tube; when a bending angle of the slide bar is small, the slide bar bended in an internal space of the articulation has a large radius of curvature; however, when the bending angle of the slide bar is large, restricted by the internal space of the articulation, the slide bar bended around the pivot pin in the internal space of the articulation has a small radius of curvature. Although it is stated in US Patent Publication No. US20090206131 and No. US20100163597 that the endoscopic surgical cutting stapler can have a joint rotation angle up to 90°, restricted by the bending deformation of the slide bar material, an actual joint rotation angle of the product is no more than 40°. The endoscopic surgical cutting stapler is restricted by an inner bore of the puncture needle. Therefore, when the pivot joint rotation angle of the end effector is no more than 40°, the end effector has a lot of dead angles when attempting to clamp the tissue. It is difficult to align the end effector with the tissue to be cut and stapled. At this time, another surgical instrument is required to enter the body cavity through another puncture needle to clamp the tissue to be cut and stapled between the staple anvil and the staple cartridge of the end effector. This requires an additional puncture needle on the human body on one hand, and adds a difficult surgery step on the other hand. Moreover, some tissue to be cut and stapled will be damaged when being pulled. Even if the tissue can be pulled, it is difficult to accurately clamp the tissue to be cut and stapled between the staple anvil and the staple cartridge of the end effector. Another disadvantage of such endoscopic surgical cutting stapler is that, when the radius of curvature of the bended slide bar is small, a radius of curvature of an inner thin plate of the slide bar is notably smaller than that of an outer thin plate. As a result, notable displacement is generated between the inner and the outer thin plates of the slide bar, and an acting force of the operating mechanism is concentrated on the inner thin plate, which significantly degrades the capability of the slide bar to pass the acting force of the operating mechanism onto the end effector, thereby affecting the capability of the end effector to clamp, fasten, cut, and staple the tissue. In addition, due to the small radius of curvature of the slide bar, the slide bar has a great resilience force, which not only increases the resistance during movement of the slide bar, but also affects placement after the joint rotation. Therefore, the articulation structure of the endoscopic surgical cutting stapler needs further improvement.

Apparently, different types of endoscopic surgical cutting staplers are designed in the prior art, and development of new endoscopic surgical cutting staplers is carried on to further improve endoscopic surgical cutting staplers massively used around the world every year, so that the end effector has a greater angle, is more accurate and more convenient in placement, and more efficient in use.

SUMMARY OF THE PRESENT INVENTION

The present invention is directed to an endoscopic surgical cutting stapler with a chain articulation, in which a joint is formed by a chain articulation, teeth are provided at two ends of a chain plate of the chain articulation, and teeth of adjacent chain plates in the same row are engaged. When an operating mechanism controls the end effector to perform joint movement, through mesh transmission of engaged teeth of the adjacent chain plates in the same row, drive motion of the operating mechanism at a distal end of an extension tube is gradually transmitted to the end effector by multiplying an angle of a most proximal chain plate of the chain articulation through several stages. The end effector is rotatable 90° with small drive motion of the operating mechanism, thereby achieving precise placement of the chain articulation after rotation. The end effector can be aligned with a part to be cut and stapled, the indicating preciseness of the angle of the end effector is increased in multiples, and the radius of curvature of the chain articulation is significantly increased.

Currently, an existing endoscopic surgical cutting stapler comprises an end effector, an articulation, an extension tube, a stapler body, and an operating mechanism. The operating mechanism is located on the stapler body, and is used to control the action of the end effector through an inner cavity of the extension tube. The end effector, the articulation, the extension tube, and the stapler body are connected in sequence. The end effector is formed by a support, a slide bar, a staple cartridge, and a staple anvil. The slide bar, the staple cartridge, and the staple anvil are mounted on the support. The staple cartridge consists of a staple cartridge housing, staple pushing blocks, a staple pushing sled, and staples. Staple slots, staple pushing holes, sled slots, and a blade pushing slot are provided in the staple cartridge housing. The staples are mounted in the staple slots. The staple pushing blocks are mounted in the staple pushing holes. The staple pushing sled is mounted in the sled slot. The staple slots and the staple pushing holes of the staple cartridge housing are aligned in rows at two sides of the blade pushing slot. An end surface of the staple anvil is provided with staple forming slots corresponding to positions of the staples in the staple cartridge, and is also provided with a cutting slot corresponding to a position of the blade pushing slot in the staple cartridge housing. The staple forming slots of the staple anvil are correspondingly aligned in rows at two sides of the cutting slot of the staple anvil. The staple slots and the staple pushing holes of the staple cartridge, and the staple forming slots of the staple anvil may be aligned in two rows, three rows, four rows, five rows, six rows, seven rows, or eight rows according to the cutting and stapling requirements of surgeries. The staple anvil may be pivoted to the support. A cutter blade may be mounted on the slide bar. The slide bar is movable in the blade pushing slot of the staple cartridge housing. A cutter blade may also be mounted in the blade pushing slot of the staple cartridge housing. When the slide bar moves in the blade pushing slot of the staple cartridge housing, the slide bar pushes the cutter blade to move in the blade pushing slot of the staple cartridge housing.

When the operating mechanism pushes the slide bar, the slide bar controls the staple anvil to pivotally rotate around the support, and controls the staple anvil and the staple cartridge to clamp or loosen the tissue to be cut and stapled. When a required gap is achieved between the staple anvil and the staple cartridge, the slide bar with two ends respectively inserted in the staple anvil and the staple cartridge of the end effector maintains a required clamping thickness of the tissue to be cut and stapled between the staple anvil and the staple cartridge. The slide bar pushes the staple pushing block through the staple pushing sled, to eject the staple from the staple cartridge through the clamped tissue to be cut and stapled and against a staple forming slot on the staple anvil, so that the U-shaped staple is deformed into a B-shaped staple, thereby stapling the tissue. A cutter blade on the slide bar cuts the clamped tissue to be cut and stapled, so as to achieve the surgery purpose of cutting the tissue.

The task of the present invention is implemented through the following technical solution:

A joint of an endoscopic surgical cutting stapler of the present invention is implemented by a chain articulation. The chain articulation consists of chain plates and pivot pins. The chain articulation is provided with a working channel extending from a proximal end to a distal end. A slide bar penetrates through the working channel of the chain articulation and performs actions of an operating mechanism. The chain plates are pivoted with each other through the pivot pins and arranged in two intersecting rows. A proximal end of a most proximal chain plate of the chain articulation is driven by the operating mechanism, and a distal end thereof is provided with teeth. Teeth are also provided on both ends of other chain plates of the chain articulation. Teeth of adjacent chain plates in the same row are engaged. The proximal end of the most proximal chain plate of the chain articulation is pivoted to an extension tube. A distal end of a most distal chain plate of the chain articulation is pivoted to the end effector. A distal end of the extension tube is provided with teeth. Teeth at a proximal end of a sub-most proximal chain plate of the chain articulation are engaged with the teeth at the distal end of the extension tube. The teeth on the chain plate may be teeth of a gear fixed on the chain plate, or shift forks fixed on the chain plate, or other types of teeth that have similar functions. The gears of the teeth on the chain plates may have the same pitch diameter, or have different pitch diameters.

The operating mechanism drives a proximal end of a first-stage chain plate at the most proximal end of the chain articulation, so that the first-stage chain plate of the chain articulation rotates around the pivot pin, thereby generating a first-stage angle. A second-stage chain plate at the sub-most proximal end is driven by the pivot pin of the first-stage chain plate and is under mesh transmission of the teeth at the distal end of the extension tube and the teeth of the second-stage chain plate. The angle of the first-stage chain plate is multiplied and transmitted to an angle of the second-stage chain plate, so that the first-stage angle is multiplied to be a second-stage angle. A third-stage chain plate is driven by the pivot pin of the second-stage chain plate and is under mesh transmission of the teeth of the first-stage chain plate and the teeth of the third-stage chain plate. The angle of the second-stage chain plate is then multiplied and transmitted to an angle of the third-stage chain plate, so that the second-stage angle is multiplied to be a third-stage angle. A fourth-stage chain plate is driven by the pivot pin of the third-stage chain plate and is under mesh transmission of the teeth of the second-stage chain plate and the teeth of the fourth-stage chain plate. The angle of the third-stage chain plate is multiplied and transmitted to an angle of the fourth-stage chain plate, so that the third-stage angle is multiplied to be a fourth-stage angle. A fifth-stage chain plate is driven by the pivot pin of the fourth-stage chain plate and is under mesh transmission of the teeth of the third-stage chain plate and the teeth of the fifth-stage chain plate. The angle of the fourth-stage chain plate is multiplied and transmitted to an angle of the fifth-stage chain plate, so that the fourth-stage angle is multiplied to be a fifth-stage angle. The rest is done in the same manner, until the end effector is driven by the pivot pin of an N-stage chain plate and is under mesh transmission of teeth of a (N−1)-stage chain plate and the teeth of the end effector, and the angle of the N-stage chain plate is multiplied and transmitted to an angle of the end effector, so that the N-stage angle is multiplied to be a (N+1)-stage angle. In this manner, when the operating mechanism controls an action of the chain articulation, transmission of the operating mechanism at the distal end of the extension tube is transformed to be the angle of the first-stage chain plate at the most proximal end of the chain articulation. Through mesh transmission of the teeth of adjacent chain plates in the same row, the angle of the first-stage chain plate is multiplied through (N+1) stages and transmitted to the angle of the end effecor.

The operating mechanism may have a rack at the distal end of the extension tube. The proximal end of the most proximal chain plate of the chain articulation may be provided with teeth. The operating mechanism drives, through the rack, the teeth at the proximal end of the most proximal chain plate of the chain articulation to rotate. A thin plate of the slide bar rotates toward two sides along with the chain articulation and is bended toward two sides.

The operating mechanism may also be provided with a gear at the distal end of the extension tube. The proximal end of the most proximal chain plate of the chain articulation may be provided with gear teeth. The operating mechanism drives, through the gear, the gear teeth at the proximal end of the most proximal chain plate of the chain articulation to rotate. A thin plate of the slide bar rotates toward two sides along with the chain articulation and is bended toward two sides.

The operating mechanism may be connected to a connecting rod at the proximal end of the most proximal chain plate of the chain articulation. The operating mechanism drives, through the connecting rod, the most proximal chain plate of the chain articulation to rotate. A thin plate of the slide bar rotates toward two sides along with the chain articulation and is bended toward two sides.

The chain plates of the endoscopic surgical cutting stapler in the present invention may be provided with a slot extending from a proximal end to a distal end of the chain articulation. The pivot pins may also be provided with a slot extending from the proximal end to the distal end of the chain articulation. The slot on the chain plates and the slot on the pivot pins form a working channel extending from the proximal end to the distal end on the chain articulation.

The chain plate may be provided with a through hole extending from the proximal end to the distal end of the chain articulation. The pivot pins may be provided with a slot extending from the proximal end to the distal end of the chain articulation. The through hole in the chain plates and the slot on the pivot pins form a working channel extending from the proximal end to the distal end on the chain articulation.

The chain plates may be provided with a slot extending from the proximal end to the distal end of the chain articulation. The pivot pins may be provided with a through hole extending from the proximal end to the distal end of the chain articulation. The slot on the chain plates and the through hole in the pivot pins form a working channel extending from the proximal end to distal end on the chain articulation.

The chain plate may be provided with a through hole extending from the proximal end to the distal end of the chain articulation. The pivot pins may be provided with a through hole extending from the proximal end to the distal end of the chain articulation. The through hole in the chain plates and the through hole in the pivot pins form a working channel extending from the proximal end to the distal end on the chain articulation.

The slide bar of the endoscopic surgical cutting stapler in the present invention may be formed by a single thin plate, or formed by multiple stacked thin plates. The thin plate forming the pushing plate may be made of various metal materials, especially a hyperelastic Ti—Ni alloy.

The slide bar may also be formed by a slide support and a pushing plate linked with each other. The pushing plate may be formed by a single thin plate, or multiple stacked thin plates. The thin plate forming the pushing plate may be made of various metal materials, especially a hyperelastic Ti—Ni alloy.

A slot extending from the proximal end to the distal end may be provided in the middle of the slide bar. A toothed portion of the chain articulation is inserted in the slot of the slide bar, so that the slide bar moves only in the working channel of the chain articulation, and is bended as the chain articulation rotates. Meanwhile, under restriction of the slot of the slide bar, the chain plates and pivot pins of the chain articulation are prevented from separation.

Both ends of the chain plate of the endoscopic surgical cutting stapler in the present invention may be provided with pin holes. The pivot pins are respectively inserted into the pin holes of the chain plates, so that the chain plates are pivoted with each other and arranged in two intersecting rows.

It is also possible that an end of the chain plate is provided with a pin hole, and the other end thereof is fixed with a pivot pin. The pivot pin fixed on each chain plate is inserted into the pin hole of another chain plate, so that the chain plates are pivoted with each other and arranged in two intersecting rows.

It is also possible that some chain plates are provided with pin holes at both ends, and other chain plates are fixed with pivot pins at both ends. The pivot pin of each chain plate with pivot pins is inserted into the pin hole of each chain plate with pin holes, so that the chain plates are pivoted with each other and arranged in two intersecting rows.

The chain articulation of the endoscopic surgical cutting stapler in the present invention may be sleeved with a shroud.

DETAILED DESCRIPTION OF THE PREFERRED EMBODIMENTS

Figure 1:
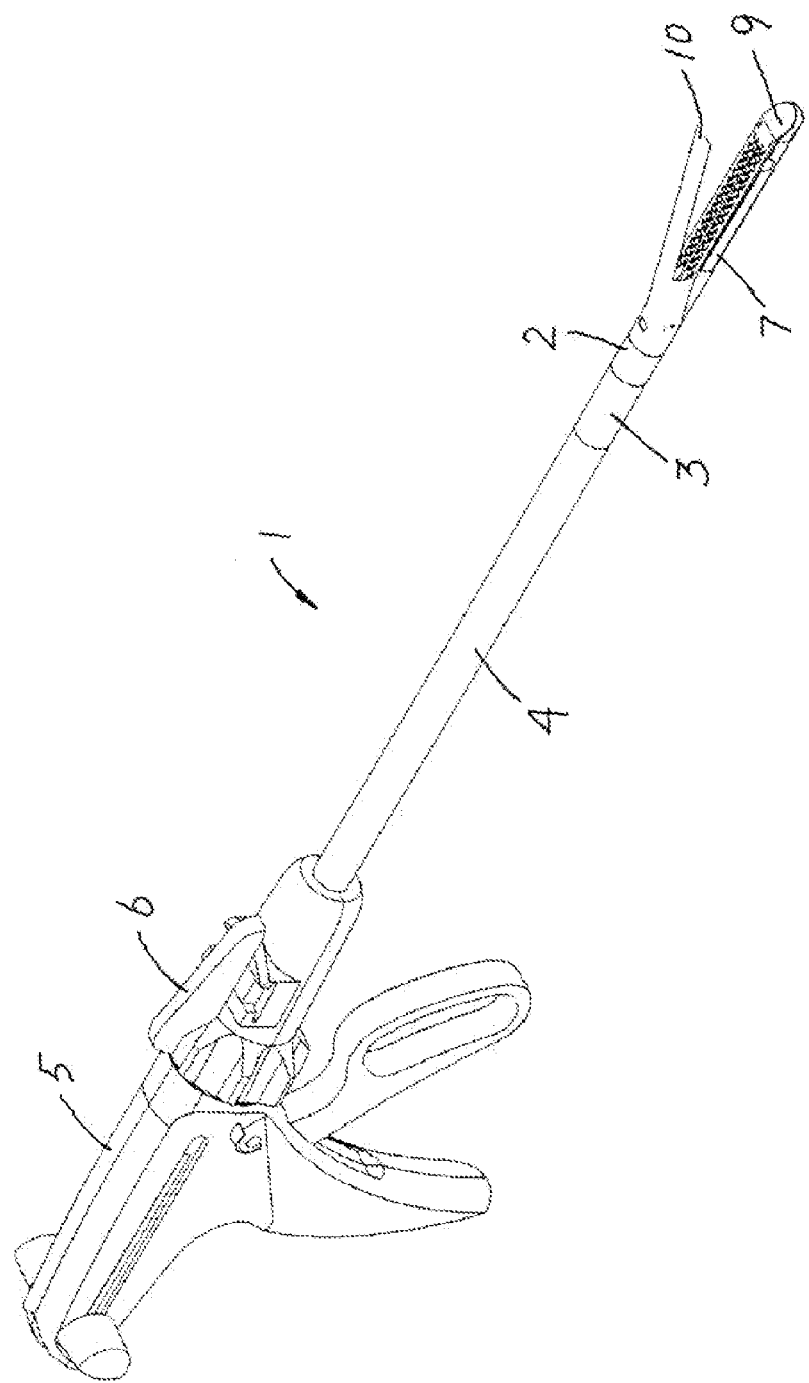
FIG. 1 is a three-dimensional outside view of an endoscopic surgical cutting stapler with a chain articulation when a staple cartridge and a staple anvil are separated in the case that the chain articulation does not rotate according to an embodiment of the present invention.
Figure 2:
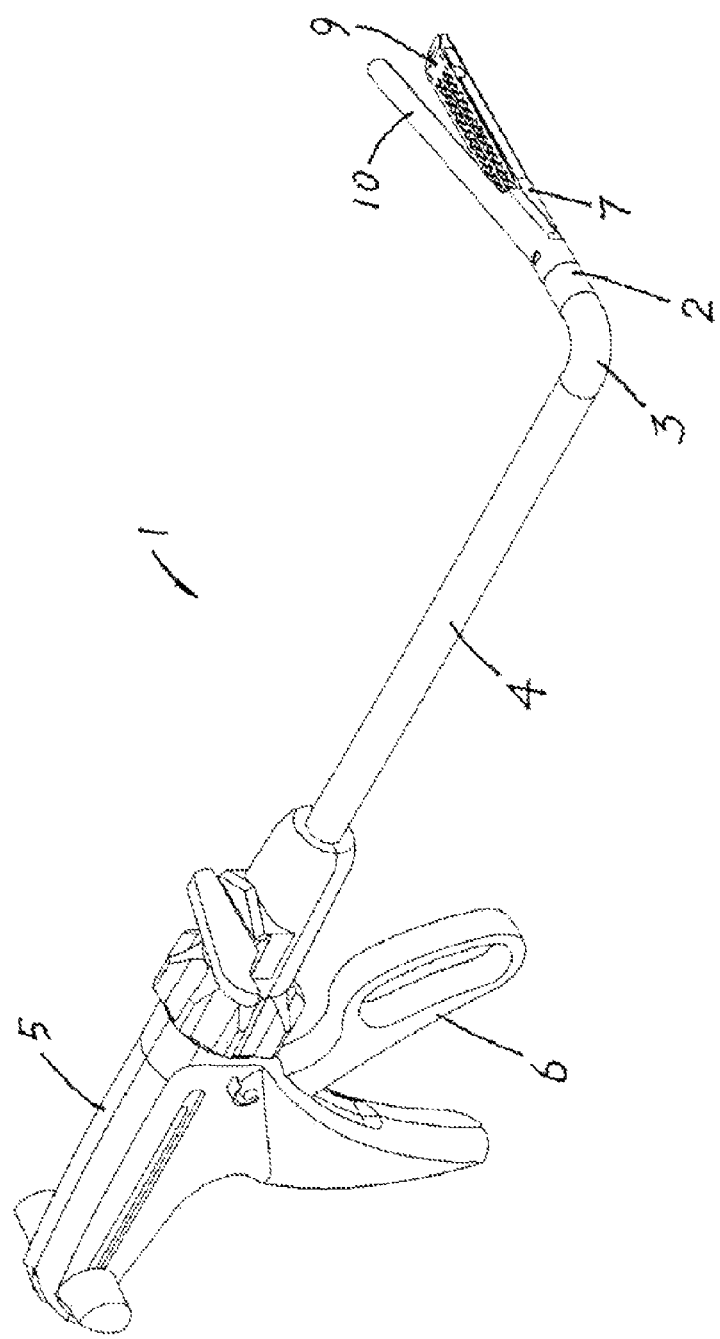
FIG. 2 is a three-dimensional outside view of the endoscopic surgical cutting stapler in FIG. 1 when the staple cartridge and the staple anvil are separated in the case that the chain articulation rotates.
Figure 3:
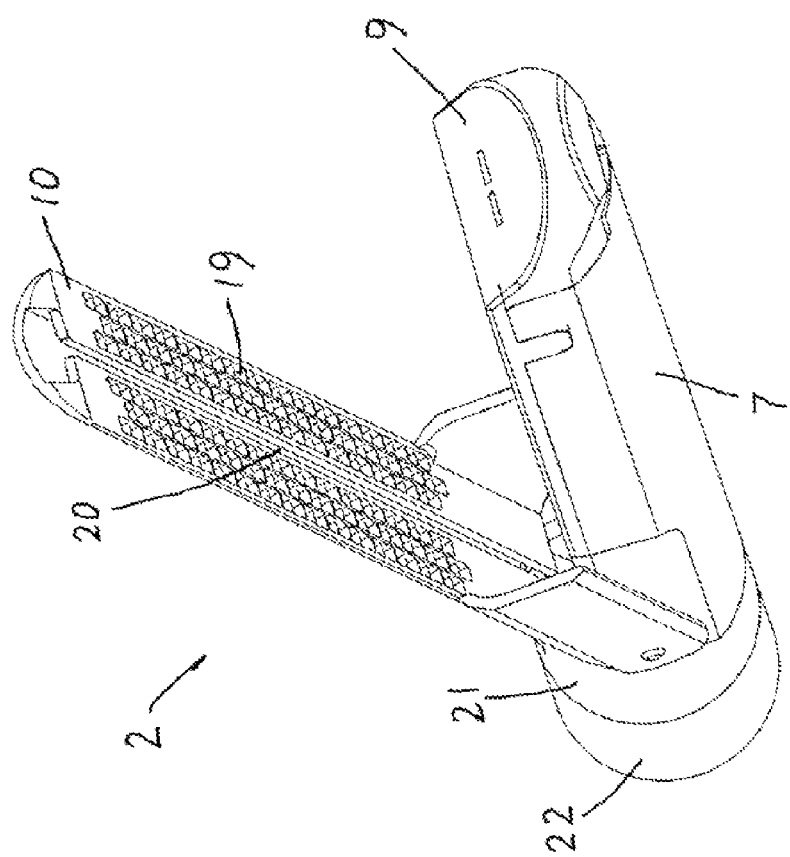
FIG. 3 is an enlarged three-dimensional outside view of an end effector with separated staple cartridge and staple anvil after a stapler body, an extension tube, a chain articulation, and an operating mechanism of an endoscopic surgical cutting stapler in FIG. 1 are removed.
Figure 4:
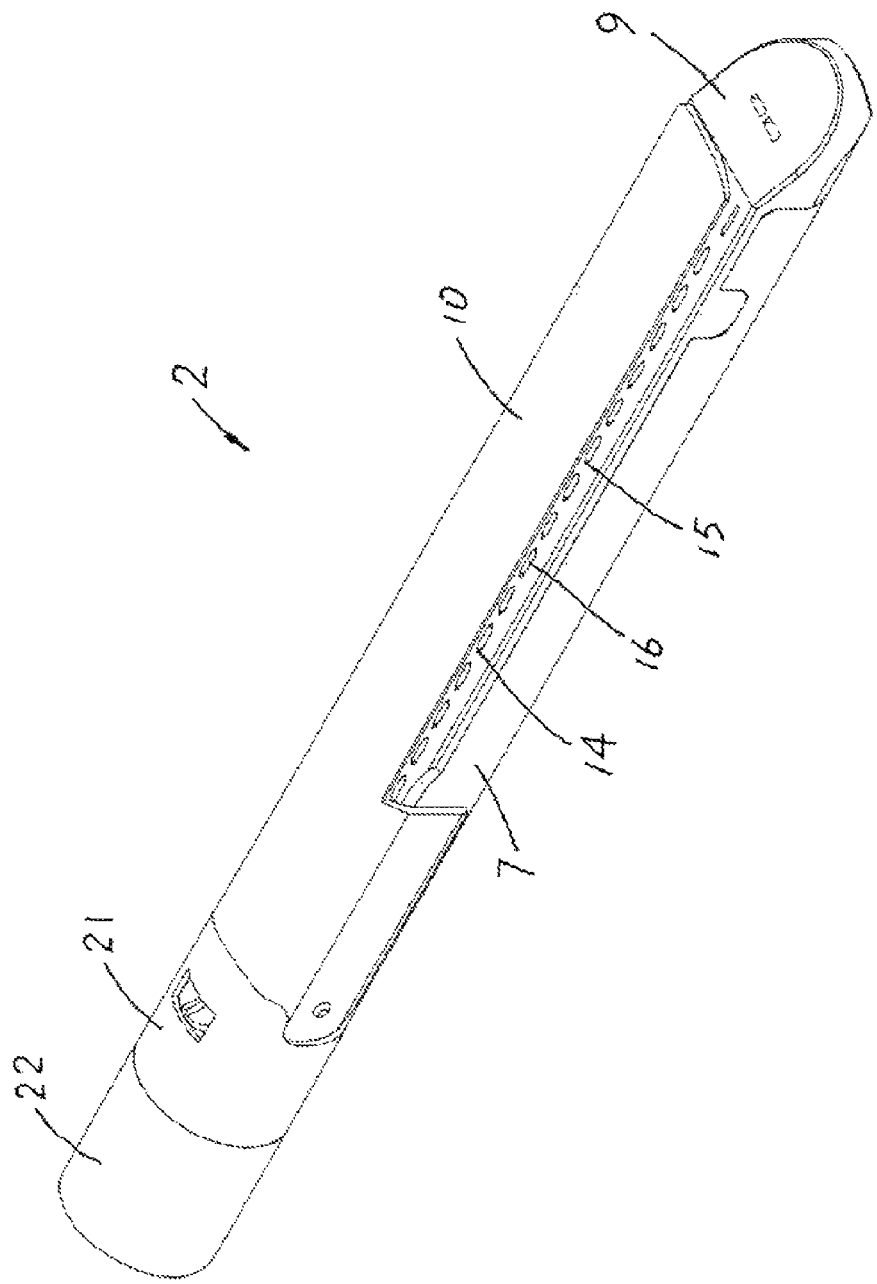
FIG. 4 is an enlarged three-dimensional outside view of an end effector in FIG. 3 when a staple cartridge and a staple anvil are closed.
Figure 5:
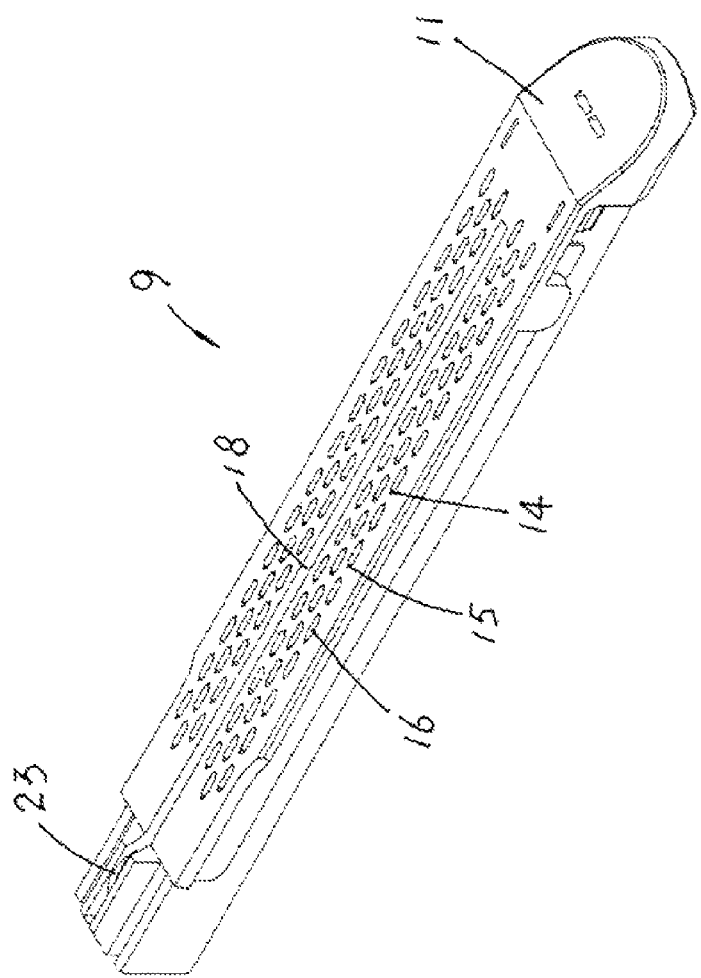
FIG. 5 is an enlarged three-dimensional outside view of an independent staple cartridge of an endoscopic surgical cutting stapler in FIG. 1.
Figure 6:
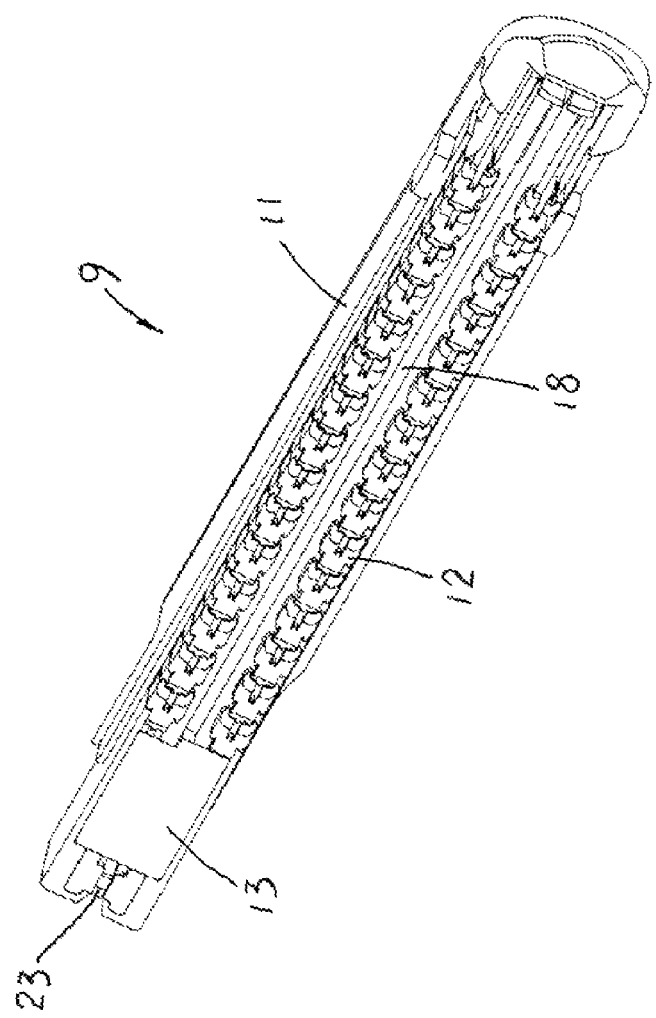
FIG. 6 is an enlarged three-dimensional outside view of a bottom portion of a staple cartridge in FIG. 5.
Figure 7:
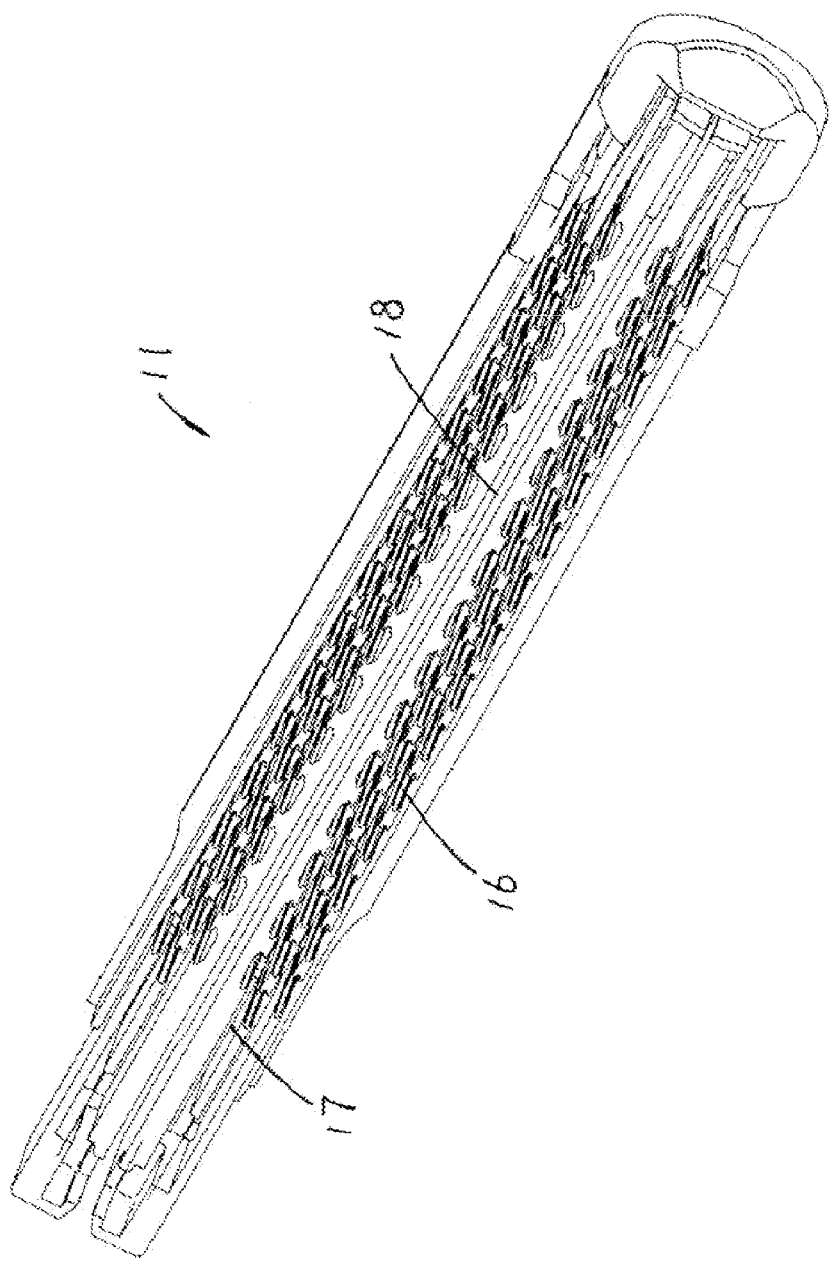
FIG. 7 is an enlarged three-dimensional outside view of a staple cartridge housing in FIG. 5.
Figure 8:
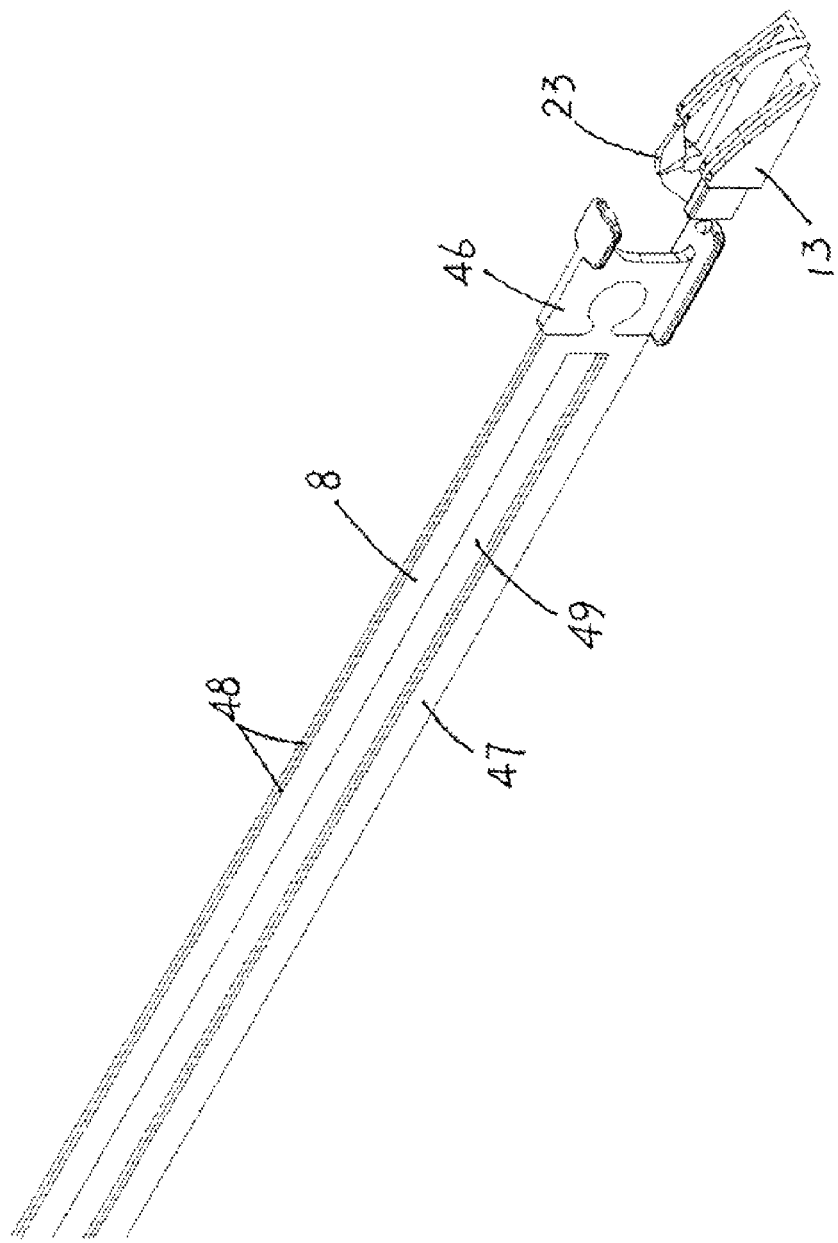
FIG. 8 is an enlarged three-dimensional outside view of a slider bar in an end effector in FIG. 1 before a slider bar pushes a cutter blade, staple pushing blocks, a staple pushing sled and staples.
Figure 9:
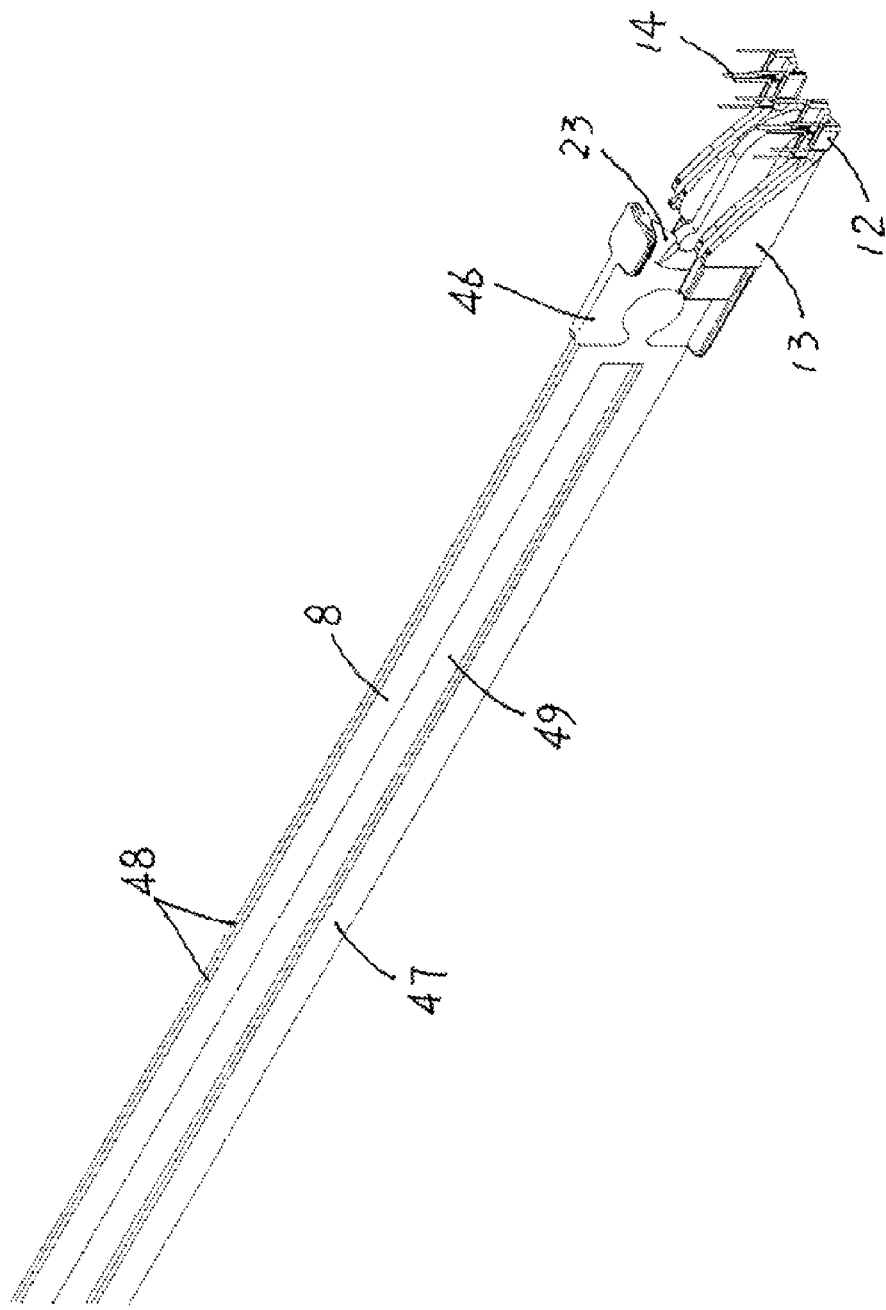
FIG. 9 is an enlarged three-dimensional outside view of a slider bar in an end effector in FIG. 1 when a slider bar pushes a cutter blade, staple pushing blocks, a staple pushing sled and staples.
Figure 10:
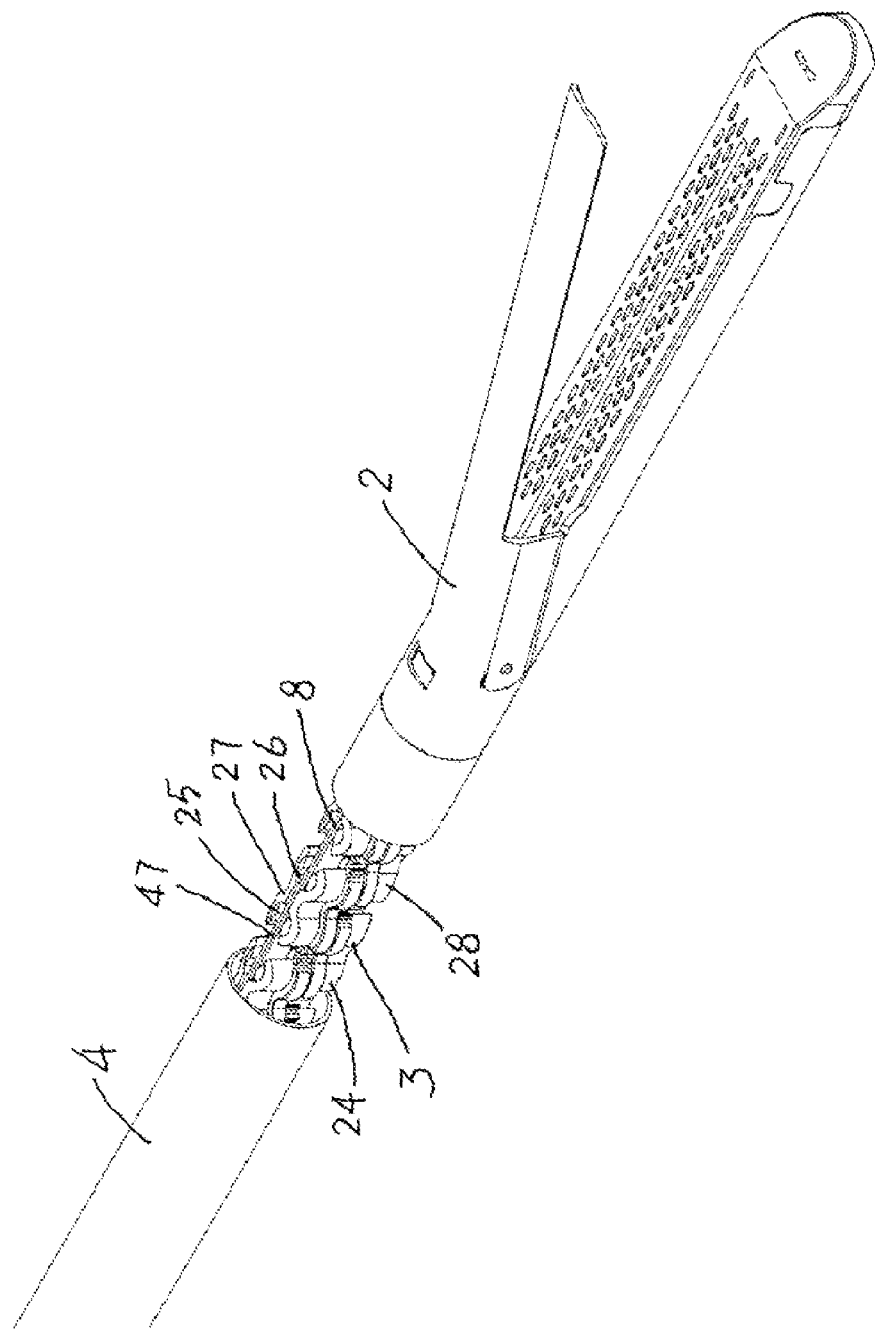
FIG. 10 is a partial enlarged three-dimensional outside view of a chain articulation, an extension tube, and an end effector in FIG. 1 when a shroud is removed from a chain articulation and the chain articulation does not rotate.
Figure 11:
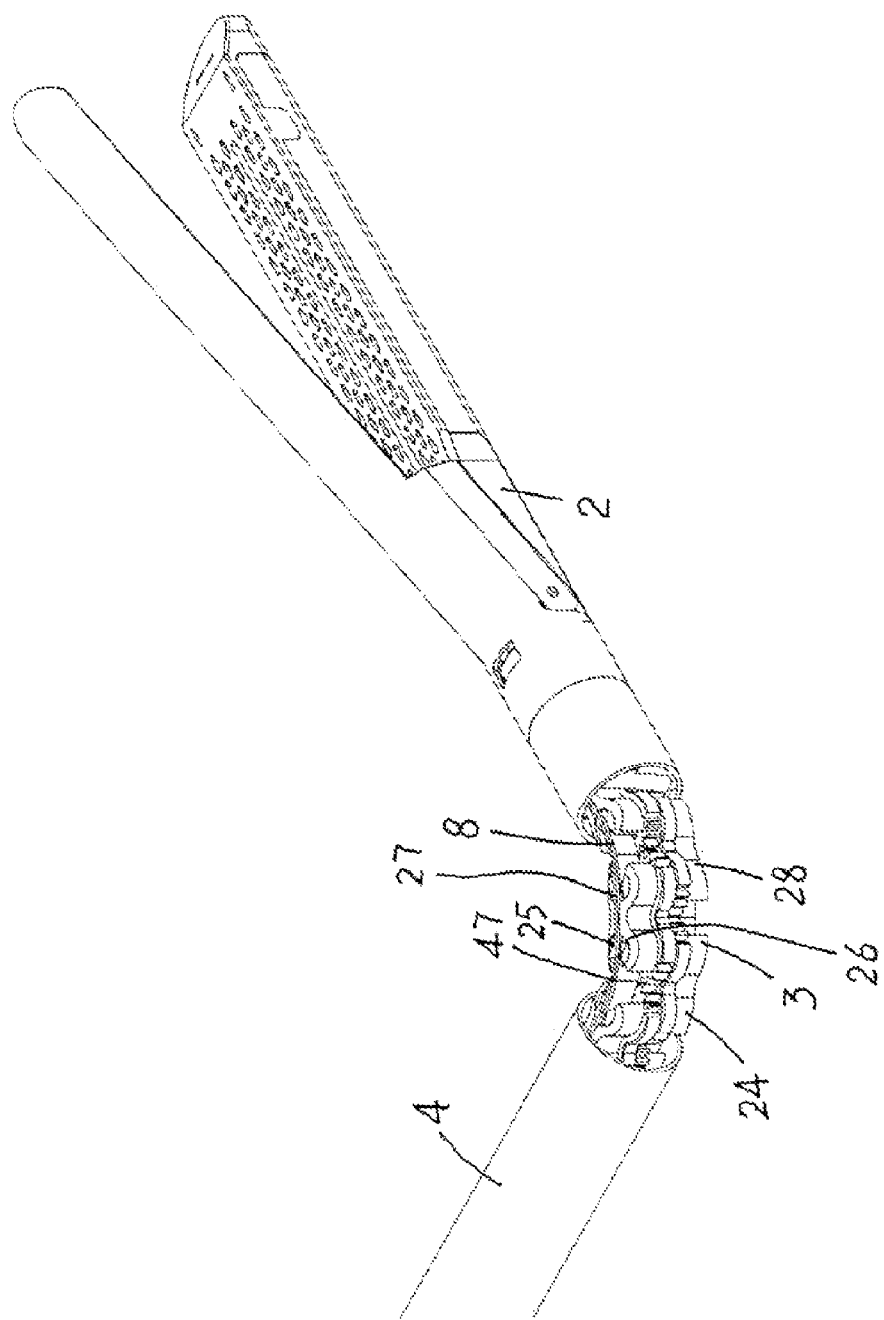
FIG. 11 is a partial enlarged three-dimensional outside view of a chain articulation, an extension tube, and an end effector when a chain articulation in FIG. 10 rotates for 90° counterclockwise.
Figure 12:
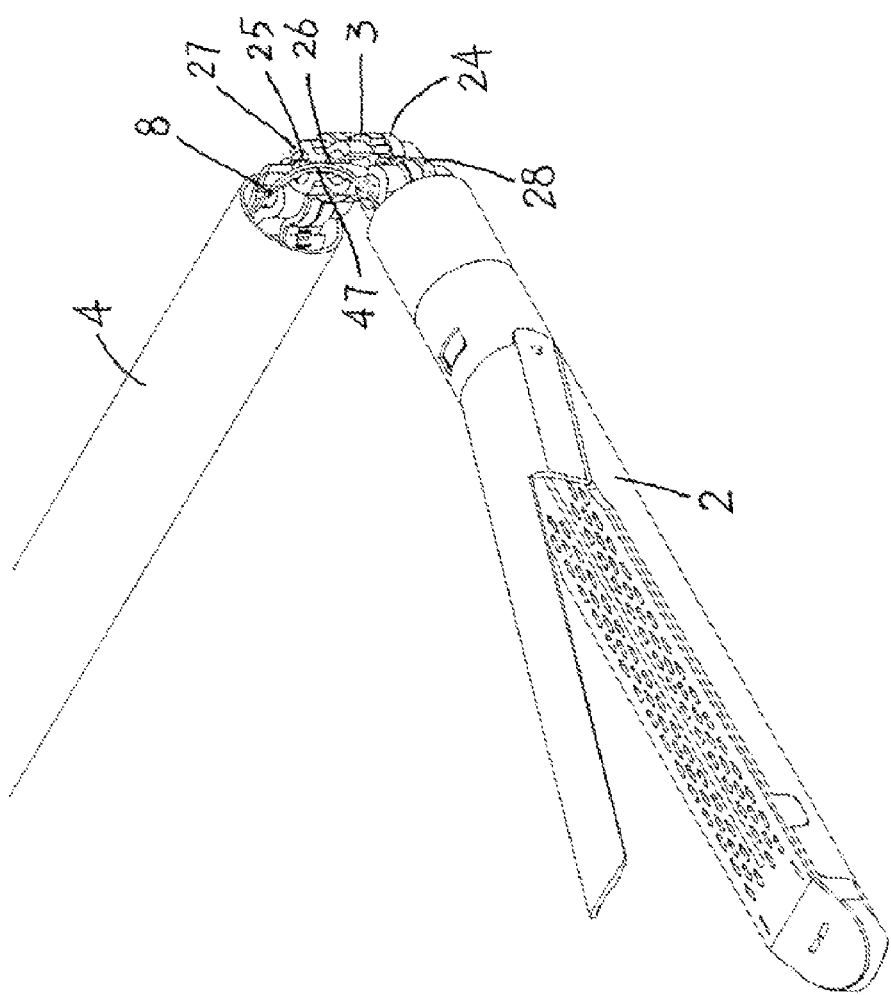
FIG. 12 is a partial enlarged three-dimensional outside view of a chain articulation, an extension tube, and an end effector when a chain articulation in FIG. 10 rotates for 90° clockwise.
Figure 13:
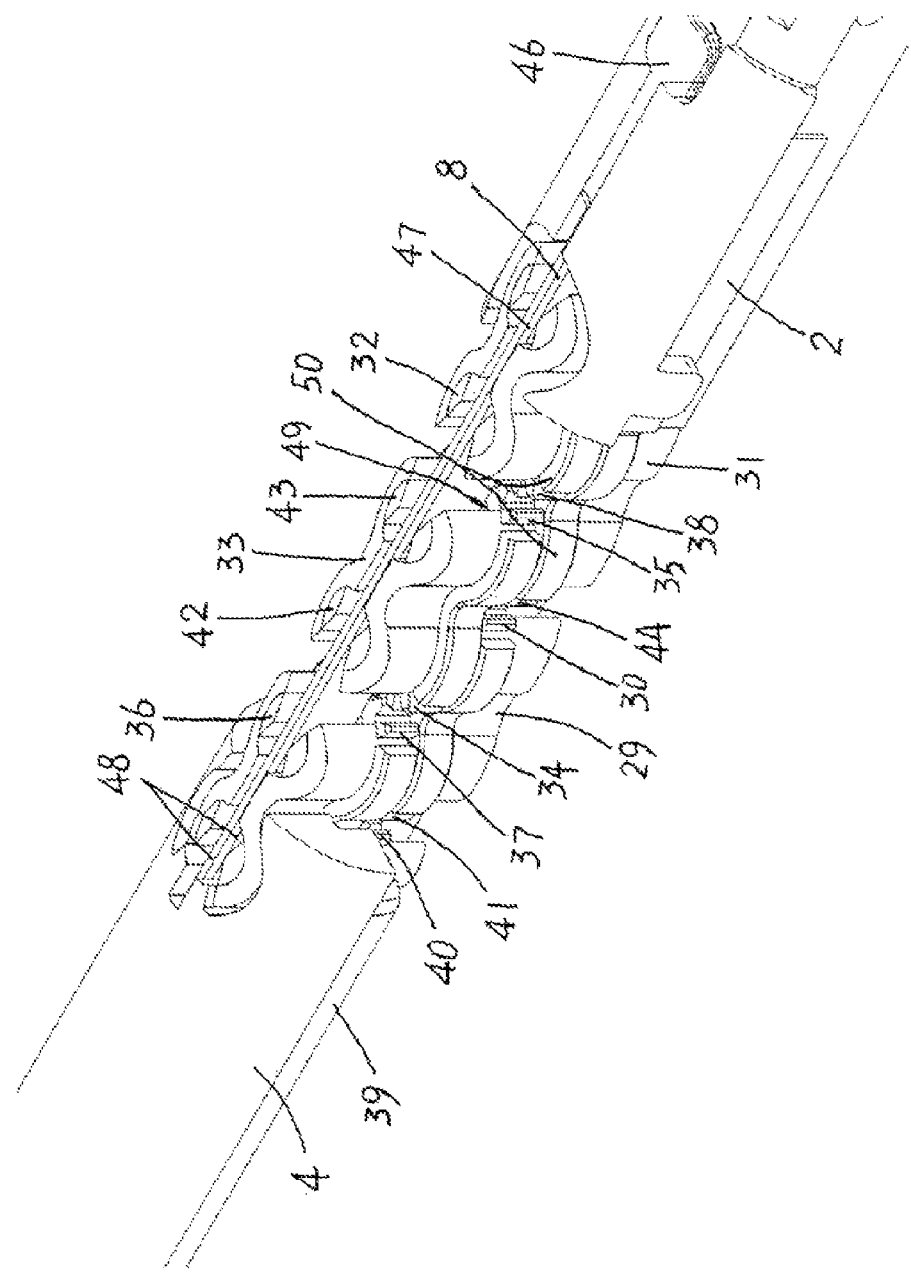
FIG. 13 is a partial enlarged three-dimensional outside view of a chain articulation, a slide bar, and accessories thereof in FIG. 1 when a shroud on the chain articulation, an end effector, and an extension tube are removed.
Figure 14:
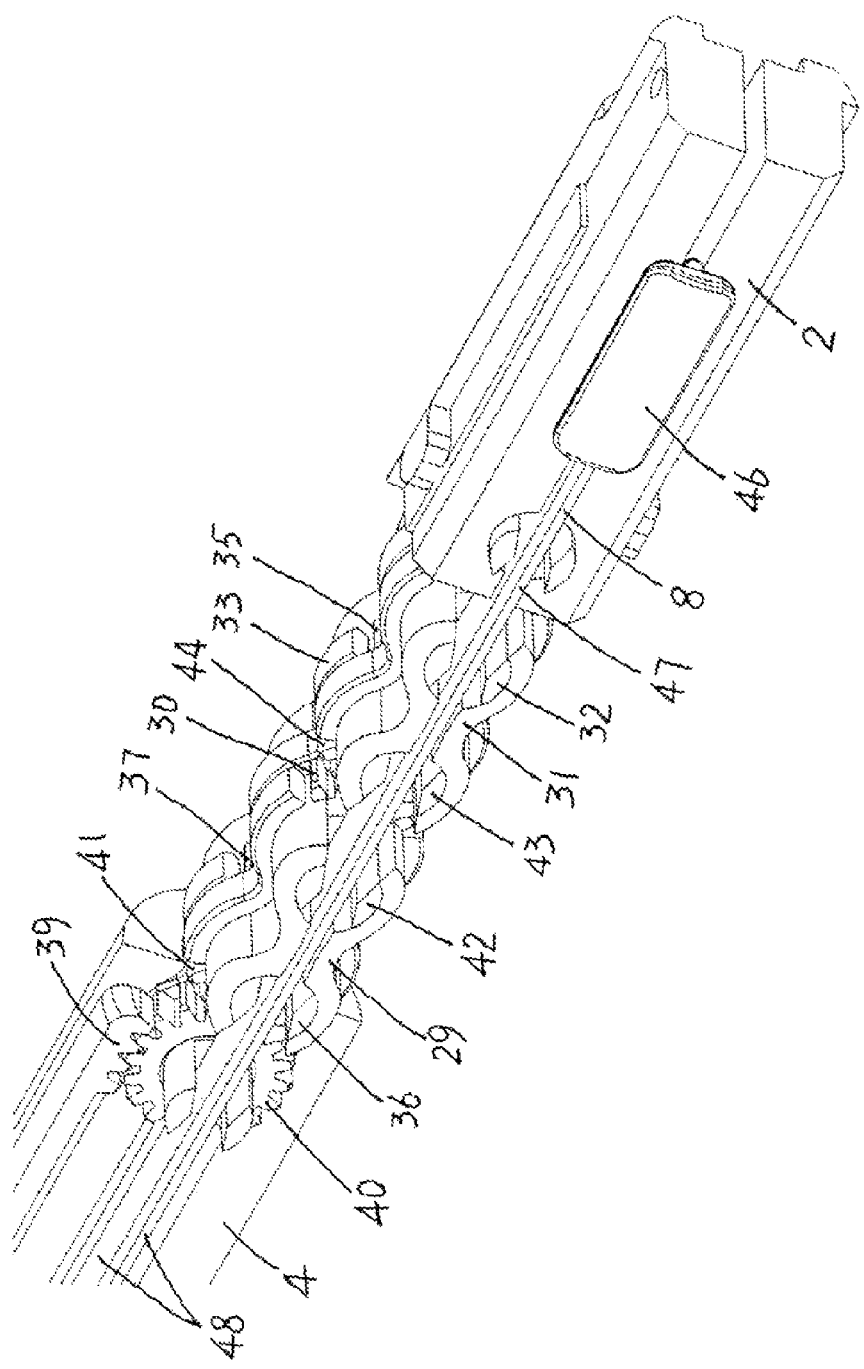
FIG. 14 is an enlarged three-dimensional outside view of a rear face of a chain articulation, a slide bar and accessories thereof in FIG. 13.
Figure 15:
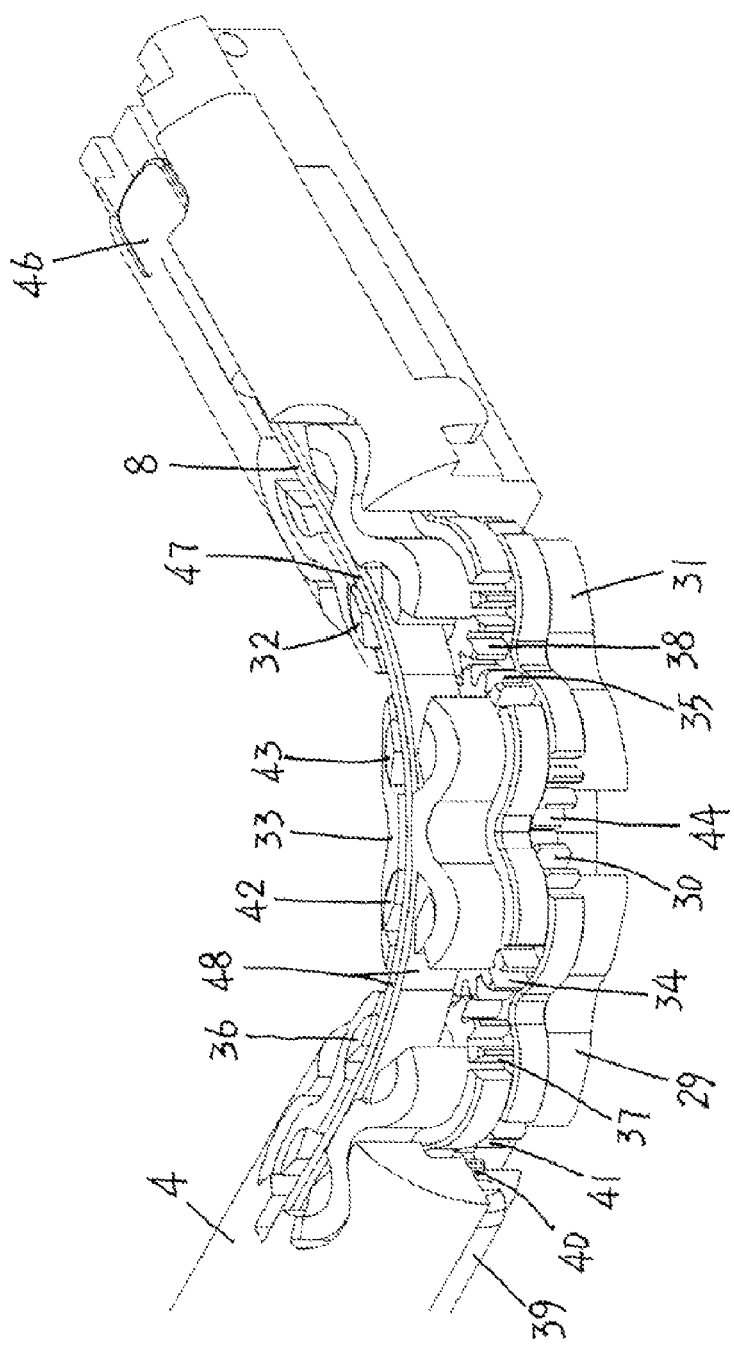
FIG. 15 is an enlarged three-dimensional outside view of a chain articulation, a slide bar and accessories thereof in FIG. 13 when the chain articulation rotates.
Figure 16:
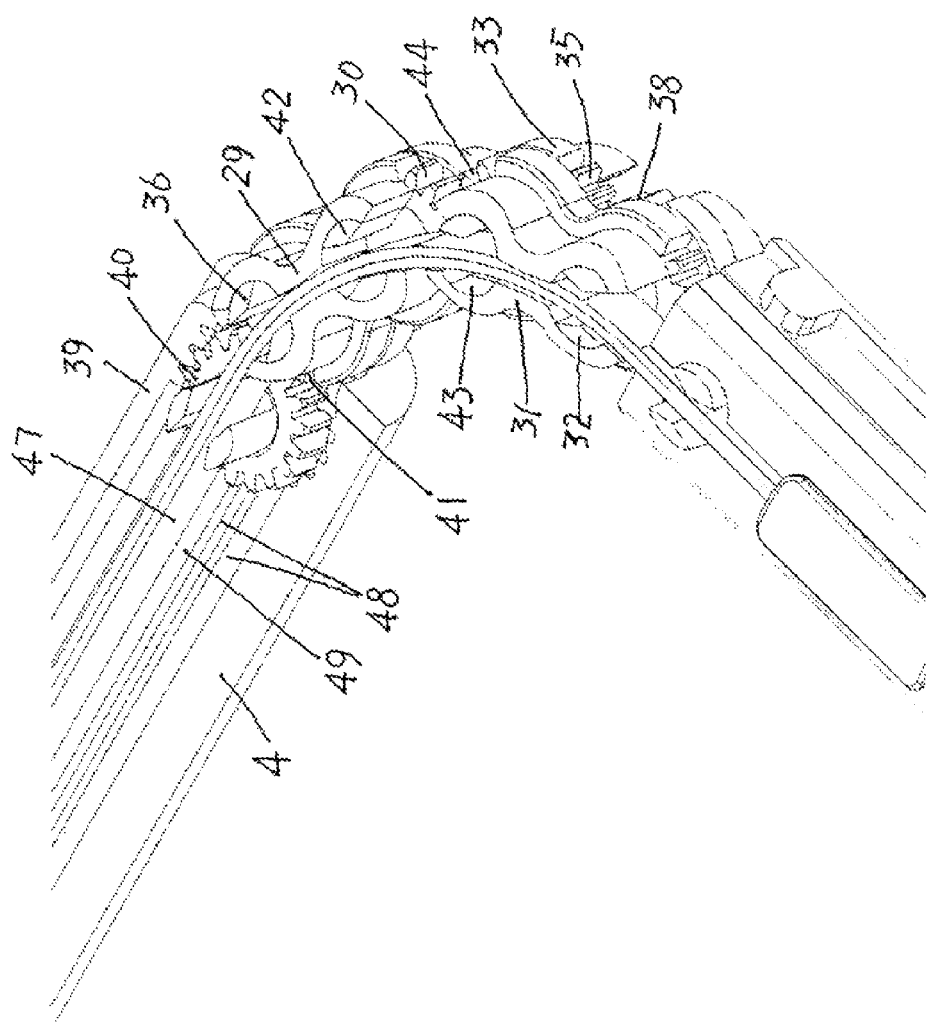
FIG. 16 is a partial enlarged three-dimensional outside view of a rear face of a chain articulation, a slide bar and accessories thereof in FIG. 15.
Figure 17:
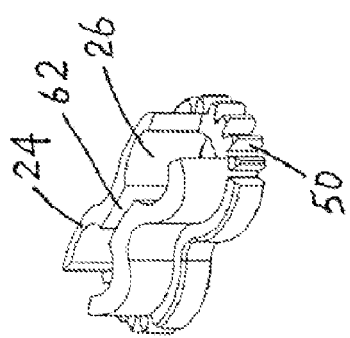
FIG. 17 is an enlarged three-dimensional outside view of a chain plate with two pin holes in a chain articulation.
Figure 18:
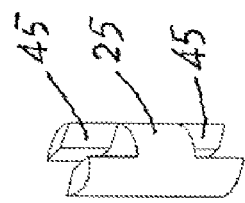
FIG. 18 is an enlarged three-dimensional outside view of a pivot pin in a chain articulation.

Exemplary embodiments of an endoscopic surgical cutting stapler with a chain articulation of the present invention are described using examples and with reference to the accompanying drawings. The scope of the present invention is subject to the claims. It should be noted that some or all of the accompanying drawings are simple drawings merely provided for illustrating the exemplary embodiments of the present invention. Therefore, actual sizes of the components are not shown in the drawings. Practical methods for achieving the above and other objectives and advantages of the present invention can be better comprehended through detailed description of the exemplary embodiments.

To emphasize the drawings and description of the chain articulation, among all components of the endoscopic surgical cutting stapler, only a link articulation and an end effector are described in detail. For the structure, installation, usage and action process of other components in the endoscopic surgical cutting stapler, reference can be made to the US patents cited in the specification.

In the accompanying drawings and following description, the term "proximal end" refers to an end close to a manipulator of the endoscopic surgical cutting stapler, and the term "distal end" refers to an end away from the manipulator of the endoscopic surgical cutting stapler. The term "end" may be an end surface or an end portion. Other direction terms may be understood according to the accompanying drawings and the following description.

Components of an endoscopic surgical cutting stapler with a chain articulation and specific implementations of the components according to the embodiments of the present invention are described with reference to FIG. 1 to FIG. 18.

As shown in FIG. 1 to FIG. 9, an endoscopic surgical cutting stapler 1 consists of an end effector 2, a chain articulation 3, an extension tube 4, a stapler body 5, and an operating mechanism 6. The operating mechanism 6 is located on the stapler body 5, and controls an action of the end effector 2 through an inner cavity of the extension tube 4 (a part of the operating mechanism 6 inside the stapler body 5 and the extension tube 4 is not shown; for details, reference may be made to the US patents cited in the specification). The end effector 2, the chain articulation 3, the extension tube 4, and the stapler body 5 are connected in sequence. The end effector 2 consists of a support 7, a slide bar 8, a staple cartridge 9, and a staple anvil 10. The slide bar 8, the staple cartridge 9, and the staple anvil 10 are mounted on the support 7. The staple cartridge 9 consists of a staple cartridge housing 11, staple pushing blocks 12, a staple pushing sled 13, and staples 14. Staple slots 15, staple pushing holes 16, sled slots 17, and a blade pushing slot 18 are provided in the staple cartridge housing 11. The staples 14 are mounted in the staple slots 15. The staple pushing blocks 12 are mounted in the staple pushing holes 16. The staple pushing sled 13 is mounted in the sled slot 17. The staple slots 15 and staple pushing holes 16 of the staple cartridge housing 11 are respectively aligned in three rows at two sides of the blade pushing slot 18. An end surface of the staple anvil 10 is provided with staple forming slots 19 corresponding to positions of the staples 14 in the staple cartridge 9, and is also provided with a cutting slot 20 corresponding to a position of the blade pushing slot 18 in the staple cartridge housing 11. The staple forming slots 19 of the staple anvil 10 are correspondingly aligned in three rows at two sides of the cutting slot 20 of the staple anvil 10. The staple anvil 10 may be pivoted to the support 7. The end effector 2 is sleeved with a neck ring 21, and the chain articulation 3 is sleeved with a shroud 22. A cutter blade 23 is mounted in the blade pushing slot 18 of the staple cartridge housing 11. When the slide bar 8 moves from a proximal end to a distal end of the staple cartridge housing 11, the slide bar 8 pushes the cutter blade 23 and the staple pushing sled 13 to move in the blade pushing slot 18 of the staple cartridge housing 11. The staple pushing sled 13 pushes the staple pushing block 12 to move in the staple pushing hole 16 through a slope, thereby forcing the staple 14 out of the staple slot 15.

As shown in FIG. 10 to FIG. 18, the chain articulation 3 consists of chain plates 24 and pivot pins 25. The chain plates 24 are provided with pin holes 26. The pivot pins 25 are respectively inserted into the pin holes 26 of the chain plates 24, so that the chain plates 24 are pivotally connected with each other and arranged in two intersecting rows 27 and 28. A proximal end of a most proximal chain plate 29 of the chain articulation 3 is driven by the operating mechanism 6, and a distal end thereof is provided with teeth 30. A distal end of a most distal chain plate 31 of the chain articulation 3 is pivoted to the end effector 2 through a pivot pin 32. Two ends of a sub-most proximal chain plate 33 of the chain articulation 3 are respectively provided with teeth 34 and 35. Teeth of adjacent chain plates in the same row are engaged. The proximal end of the most proximal chain plate 29 of the chain articulation 3 is pivoted to the extension tube 4 through the pivot pin 36. A distal end of the extension tube 4 is provided with teeth 37. A proximal end of the end effector 2 is provided with teeth 38. The teeth 34 of at the proximal end of the sub-most proximal chain plate 33 of the chain articulation 3 are engaged with the teeth 37 at the distal end of the extension tube 4. The teeth 35 at the distal end of the chain plate 33 are engaged with the teeth 38 at the proximal end of the end effector 2. Teeth on each chain plate 24 are gear teeth.

The operating mechanism 6 is provided with a rack 39 and a gear 40 that are engaged with each other at the distal end of the extension tube 4. The proximal end of the most proximal chain plate 29 of the chain articulation 3 may be provided with gear teeth 41. The gear 40 is engaged with the gear teeth 41 of the chain plate 29. The operating mechanism 6 drives the gear 40 through the rack 39, thereby driving the gear teeth 41 at the proximal end of the most proximal chain plate 29 of the chain articulation 3 to rotate. The chain plate 33 is driven by the pivot pin 42 of the chain plate 29 and is under mesh transmission of the teeth 37 at the distal end of the extension tube 4 and the teeth 34 of the chain plate 33 that are engaged; then, an angle of the chain plate 29 is multiplied and transmitted to an angle of the chain plate 33. The chain plate 31 is driven by the pivot pin 43 of the chain plate 33 and is under mesh transmission of the teeth 30 of the chain plate 29 and the teeth 44 of the chain plate 31 that are engaged; then, the angle of the chain plate 33 is multiplied and transmitted to an angle of the chain plate 31. The end effector 2 is driven by the pivot pin 32 of the chain plate 31 and is under mesh transmission of the teeth 35 of the chain plate 33 and the teeth 38 of the end effector 2 that are engaged; then, the angle of the chain plate 31 is further multiplied and transmitted to an angle of the end effector 2. In this way, when the operating mechanism 6 controls the end effector 2 to perform joint movement, through mesh transmission of engaged teeth of adjacent chain plates in the same row, drive motion of the operating mechanism 6 at the distal end of the extension tube 4 is transmitted to the end effector 2 by multiplying the angle of the most proximal plate 29 of the chain articulation 3 through four stages. The end effector 2 then obtains an angle quadruple of the angle of the chain plate 29.

The chain plates 24 may be provided with a slot 62 extending from the proximal end to the distal end of the chain articulation 3. The pivot pins 25 are provided with a slot 45 extending from the proximal end to the distal end of the chain articulation 3. The slot 62 on the chain plates 24 and the slot 45 on the pivot pins 25 form a working channel extending from the proximal end to the distal end on the chain articulation 3. The slide bar 8 penetrates through the slot 62 on the chain plates 24 and the slot 45 on the pivot pins 25.

As shown in FIG. 8 to FIG. 18, the slide bar 8 is formed by a slide support 46 and a pushing plate 47 that are linked with each other. The pushing plate 47 is formed by two stacked thin plates 48. A slot 49 extending from the proximal end to the distal end is provided in the middle of the slide bar 8. A toothed portion 50 of the chain articulation 3 is inserted in the slot 49 of the slide bar 8, so that the slide bar 8 moves only in the working channel of the chain articulation 3, and is bended as the chain articulation 3 rotates. Meanwhile, under restriction of the slot 49 of the slide bar 8, the chain plates 24 and pivot pins 25 of the chain articulation 3 are prevented from separation.

Figure 19:
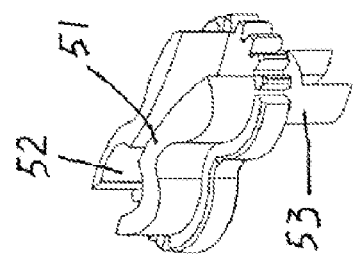
FIG. 19 is an enlarged three-dimensional outside view of a chain plate with a single pin hole and a single pivot pin in a chain articulation.

As shown in FIG. 19, in another embodiment, one end of a chain plate 51 is provided with a pin hole 52, and the other end is provided with a pivot pin 53. The pivot pin 53 fixed on each chain plate 51 is inserted into the pin hole 52 of another chain plate, so that the chain plates 51 are pivoted with each other and arranged in two intersecting rows.

Figure 20:
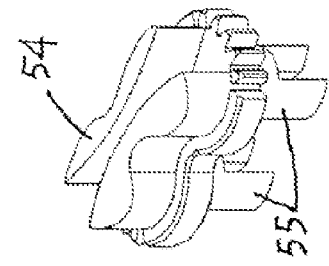
FIG. 20 is an enlarged three-dimensional outside view of a chain plate with two pivot pins in a chain articulation.

As shown in FIG. 20, in still another embodiment, pivot pins 55 are fixed on both ends of a chain plate 54. The pivot pins 55 fixed on the chain plate 54 are respectively inserted into the pin holes 25 of the chain plate 24, so that the chain plates 54 and the chain plates 24 are pivoted with each other and arranged in two intersecting rows.

Figure 21:
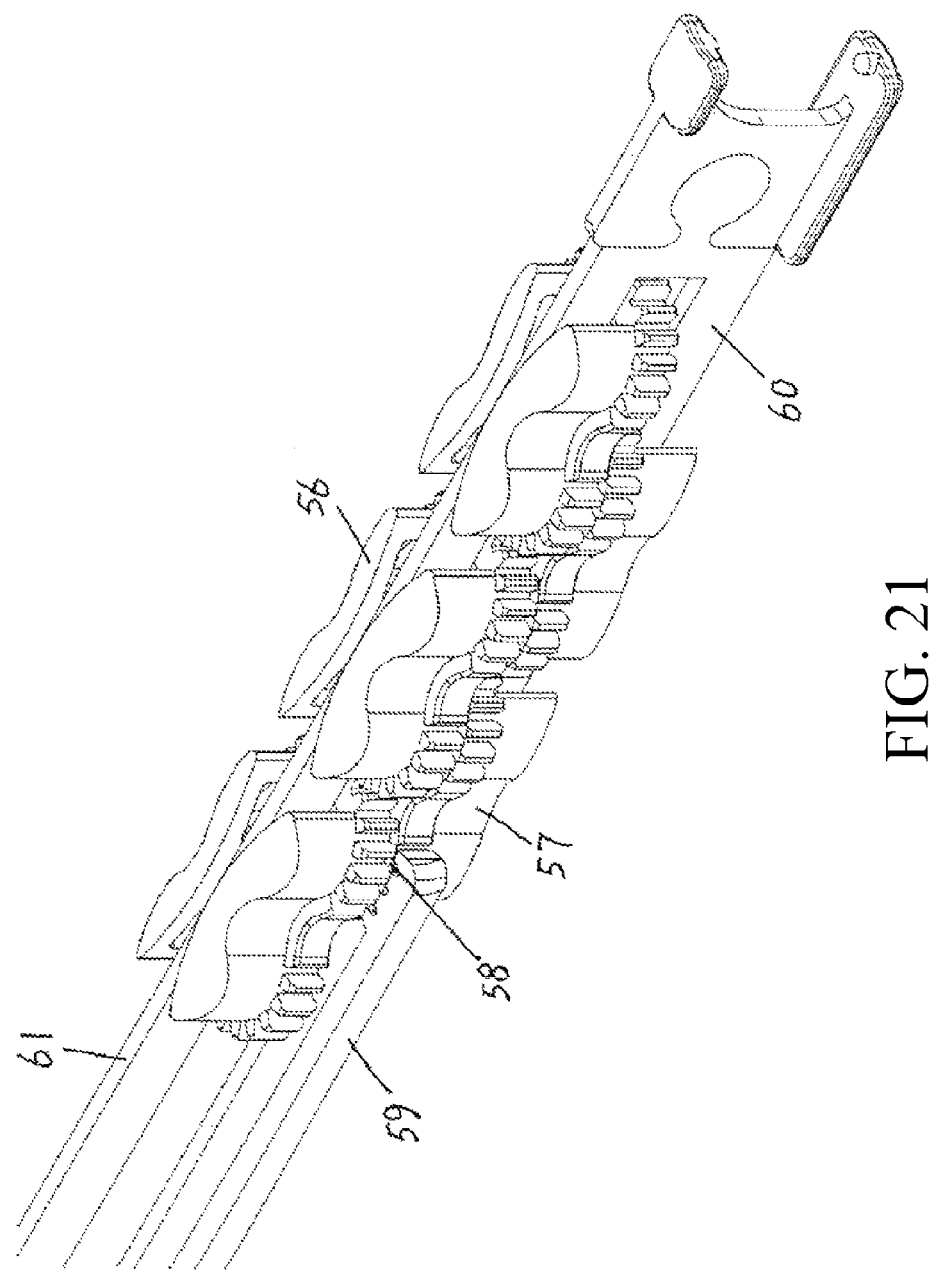
FIG. 21 is a partial enlarged three-dimensional outside view of another chain articulation, another slide bar and accessories thereof in FIG. 1.

As shown in FIG. 21, teeth 58 are provided at a proximal end of a most proximal chain plate 57 of a chain articulation 56. The operating mechanism 6 drives, through a rack 59, the teeth 58 at the proximal end of the most proximal chain plate 57 of the chain articulation 56 to rotate. When the operating mechanism 6 controls the end effector 2 to perform joint movement, through mesh transmission of engaged teeth of adjacent chain plates in the same row, drive motion of the operating mechanism 6 at the distal end of the extension tube 4 is transmitted to the end effector 2 by gradually multiplying the angle of the most proximal chain plate 57 of the chain articulation 56 through several stages. This process is similar to that described in FIG. 10 to FIG. 18. The single thin plate 61 of the slide bar 60 is bended toward two sides as the chain articulation 56 rotates toward two sides.

According to the above detailed description, the endoscopic surgical cutting stapler with a chain articulation in the present invention has the following technical effects:

When the endoscopic surgical cutting stapler is used in aparoscopic surgeries or thoracoscopic surgeries, an end effector first enters a body cavity through a puncture needle with an inner diameter of 12 mm to 13 mm. Then the end effector is controlled to perform axial rotation and joint rotation, so as to be aligned with tissue to be cut and stapled. The tissue to be cut and stapled is clamped, fastened, and loosened through the staple anvil and the staple cartridge of the end effector, thereby achieving the surgery purpose of cutting and stapling the tissue. In use of the endoscopic surgical cutting stapler, if the end effector fails to be aligned with the tissue to be cut and stapled, the end effector cannot clamp the tissue to be cut and stapled between the staple anvil and the staple cartridge, and cannot perform cutting and stapling operations.

In an existing endoscopic surgical cutting stapler, the end effector and the extension tube are jointed through a pivot pin. The slide bar is formed by stacked thin plates. The end effector is pulled by a pull rod extending from the extension tube and sleeved on the end effector, thereby controlling the end effector to perform joint rotation around the pivot pin and relative to the extension tube. The thin plates of the slide bar rotate toward two sides along with the articulation and are bended toward the two sides. Such endoscopic surgical cutting stapler has the following disadvantage: restricted by the pivot pin, the end effector can only perform joint rotation around the pivot pin and relative to the extension tube. When a bending angle of the slide bar is small, the slide bar bended in an internal space of the articulation has a large radius of curvature. However, when the bending angle of the slide bar is large, restricted by the internal space of the articulation, the slide bar bended around the pivot pin in the internal space of the articulation has a small radius of curvature. Therefore, the joint rotation angle is no more than 40°. The endoscopic surgical cutting stapler is restricted by an inner bore of the puncture needle. Therefore, when the joint rotation angle of the pivot of the end effector is no more than 40°, the end effector has a lot of dead angles when attempting to clamp the tissue. It is difficult to align the end effector with the tissue to be cut and stapled. At this time, another surgical instrument needs to be used to enter the body cavity through another puncture needle to clamp the tissue to be cut and stapled between the staple anvil and staple cartridge of the end effector. This requires an additional puncture needle on the human body on one hand, and adds a difficult surgery step on the other hand. Moreover, some tissue to be cut and stapled will be damaged when being pulled. Even if the tissue can be pulled, it is difficult to accurately clamp the tissue to be cut and stapled between the staple anvil and staple cartridge of the end effector. Another disadvantage of such endoscopic surgical cutting stapler is that, when the radius of curvature of the bended slide bar is small, a radius of curvature of an inner thin plate of the slide bar is notably smaller than that of an outer thin plate. As a result, notable displacement is generated between the inner and the outer thin plates of the slide bar, and an acting force of the operating mechanism is concentrated on the inner thin plate, which significantly degrades the capability of the slide bar to pass the acting force of the operating mechanism onto the end effector, thereby affecting the capability of the end effector to clamp, fasten, cut and staple the tissue. In addition, due to the small radius of curvature of the slide bar, the slide bar has a great resilience force, which not only increases the resistance during movement of the slide bar, but also affects placement after the joint rotation. Therefore, the existing articulation structure of the endoscopic surgical cutting stapler needs further improvement.

The operating mechanism of the endoscopic surgical cutting stapler with a chain articulation according to the present invention drives the proximal end of a first-stage chain plate at the most proximal end of the chain articulation, so that the first-stage chain plate of the chain articulation rotates around the pivot pin, thereby generating a first-stage angle. A second-stage chain plate at the sub-most proximal end is driven by the pivot pin of the first-stage chain plate and is under mesh transmission of the teeth at the distal end of the extension tube and the teeth of the second-stage chain plate. The angle of the first-stage chain plate is multiplied and transmitted to an angle of the second-stage chain plate, so that the first-stage angle is multiplied to be a second-stage angle. A third-stage chain plate is driven by the pivot pin of the second-stage chain plate and is under mesh transmission of the teeth of the first-stage chain plate and the teeth of the third-stage chain plate. The angle of the second-stage chain plate is then multiplied and transmitted to an angle of the third-stage chain plate, so that the second-stage angle is multiplied to be a third-stage angle. A fourth-stage chain plate is driven by the pivot pin of the third-stage chain plate and is under mesh transmission of the teeth of the second-stage chain plate and the teeth of the fourth-stage chain plate. The angle of the third-stage chain plate is multiplied and transmitted to an angle of the fourth-stage chain plate, so that the third-stage angle is multiplied to be a fourth-stage angle. The fifth-stage chain plate is driven by the pivot pin of the fourth-stage chain plate and is under mesh transmission of the teeth of the third-stage chain plate and the teeth of the fifth-stage chain plate. The angle of the fourth-stage chain plate is multiplied and transmitted to an angle of the fifth-stage chain plate, so that the fourth-stage angle is multiplied to be a fifth-stage angle. The rest is done in the same manner, until the end effector is driven by the pivot pin of an N-stage chain plate and is under mesh transmission of teeth of a (N−1)-stage chain plate and the teeth of the end effector, and the angle of the N-stage chain plate is multiplied and transmitted to an angle of the end effector, so that the N-stage angle is multiplied to be a (N+1)-stage angle. In this manner, when the operating mechanism controls an action of the chain articulation, transmission of operating mechanism at the distal end of the extension tube is transformed to be the angle of the first-stage chain plate at the most proximal end of the chain articulation. Through mesh transmission of the teeth of adjacent chain plates in the same row, the angle of the first-stage chain plate is multiplied through (N+1) stages and transmitted to the angle of the end effecor.

On the condition that chain plates at different stages have the same number of teeth, the end effector can obtain an angle that is (N+1) times of the angle of the first-stage chain plate at the most proximal end of the chain articulation. If the number N of the chain plates of the chain articulation increases, the value of (N+1) increases and the angle transmitted to the end effector is multiplied by more times. If the number N of the chain plates of the chain articulation decreases, the value of (N+1) decreases and the angle transmitted to the end effector is multiplied by less times. On the condition that chain plates at different stages have different numbers of teeth, the angle of the first-stage chain plate at the most proximal end of the chain articulation is multiplied by different times and transmitted to an angle of the end effector. In this manner, the present invention achieves the following technical effect: the chain articulation is capable of bending in a large scale and with a great curvature toward two sides, implements precise placement, and has sufficient rigidity at any bending position, so that the end effector is precisely aligned with the part to be cut and stapled.

In another aspect, the chain articulation is formed by multiple stages of chain plates. Therefore, when the end effector rotates, the radius of curvature of the bended chain articulation is significantly greater than that of the single pivot pin rotation in the prior art, enabling the radius of curvature of bending deformation of the slide bar in the articulation to be also increased. In this manner, the present invention achieves the following technical effect: even if the angle of the end effector is as great as 90°, the inner and the outer thin plates of the slide bar have small displacement, and only a little proportion of the acting force that the operating mechanism transmits to the end effector through the slide bar is lost.

What is claimed is:

1. An endoscopic surgical cutting stapler with a chain articulation, comprising: an end effector, a chain articulation, an extension tube, a stapler body, and an operating mechanism, wherein the operating mechanism is located on the stapler body, the operating mechanism controls an action of the end effector through an inner cavity of the extension tube; the end effector, the chain articulation, the extension tube, and the stapler body are connected in sequence;

the end effector is formed by a support, a slide bar, a staple cartridge, and a staple anvil; the slide bar, the staple cartridge, and the staple anvil are mounted on the support; the staple cartridge is formed by a staple cartridge housing, staple pushing blocks, a staple pushing sled, and staples; the staple cartridge housing is provided with staple slots, staple pushing holes, a sled slot, and a blade pushing slot; the staples are mounted in the staple slots; the staple pushing blocks are mounted in the staple pushing holes; the staple pushing sled is mounted in the sled slot; the staple slots and the staple pushing holes of the staple cartridge housing are aligned at two sides of the blade pushing slot; an end surface of the staple anvil is provided with staple forming slots corresponding to positions of the staples in the staple cartridge, and is also provided with a cutting slot corresponding to a position of the blade pushing slot in the staple cartridge housing;

the chain articulation is formed by chain plates and pivot pins; a working channel is provided from a proximal end to a distal end on the chain articulation; the slide bar penetrates through the working channel of the chain articulation and performs an action of the operating mechanism; the chain plates are pivoted with each other through the pivot pins and arranged in two intersecting rows; a proximal end of a most proximal chain plate of the chain articulation is driven by the operating mechanism, and a distal end thereof is provided with teeth; teeth are provided on both ends of other chain plates of the chain articulation; teeth of adjacent chain plates in the same row are engaged; the proximal end of the most proximal chain plate of the chain articulation is pivoted to the extension tube; a distal end of a most distal chain plate of the chain articulation is pivoted to the end effector; a distal end of the extension tube is provided with teeth; teeth at a proximal end of a sub-most proximal chain plate of the chain articulation are engaged with the teeth at the distal end of the extension tube.

2. The endoscopic surgical cutting stapler with a chain articulation as in claim 1, wherein a slot extending from a proximal end to a distal end is provided in the middle of the slide bar; a toothed portion of the chain articulation is inserted in the slot of the slide bar, so that the slide bar moves only in the working channel of the chain articulation, and is bended as the chain articulation rotates; meanwhile, under restriction of the slot of the slide bar, the chain plates and pivot pins of the chain articulation are prevented from separation.

3. The endoscopic surgical cutting stapler with a chain articulation as in claim 1, wherein the teeth on the chain plate are teeth of a gear fixed on the chain plate.

4. The endoscopic surgical cutting stapler with a chain articulation as in claim 1, wherein the operating mechanism is provided with a rack at the distal end of the extension tube; the proximal end of the most proximal chain plate of the chain articulation is provided with gear teeth; the rack of the operating mechanism at the distal end of the extension tube are engaged with the gear teeth at the proximal end of the most proximal chain plate of the chain articulation; the operating mechanism drives, through the rack, the gear teeth at the proximal end of the most proximal chain plate of the chain articulation, so as to drive the most proximal chain plate of the chain articulation to rotate, so that the end effector rotates toward two sides.

5. The endoscopic surgical cutting stapler with a chain articulation as in claim 1, wherein the operating mechanism is provided with a gear at the distal end of the extension tube; the proximal end of the most proximal chain plate of the chain articulation is provided with gear teeth; the gear of the operating mechanism at the distal end of the extension tube is engaged with the gear teeth at the proximal end of the most proximal chain plate of the chain articulation; the operating mechanism drives, through the gear, the gear teeth at the proximal end of the most proximal chain plate of the chain articulation, so as to drive the most proximal chain plate of the chain articulation to rotate, so that the end effector rotates toward two sides.

6. The endoscopic surgical cutting stapler with a chain articulation as in claim 1, wherein the chain plates are provided with a slot extending from the proximal end to the distal end of the chain articulation; the pivot pins are provided with a slot extending from the proximal end to the distal end of the chain articulation; the slot on the chain plates and the slot on the pivot pins form the working channel extending from the proximal end to the distal end on the chain articulation.

7. The endoscopic surgical cutting stapler with a chain articulation as in claim 1, wherein both ends of the chain plate are provided with pin holes, the pivot pins are respectively inserted into the pin holes of the chain plates, so that the chain plates are pivoted with each other through pivot pins and arranged in two intersecting rows.

8. The endoscopic surgical cutting stapler with a chain articulation as in claim 1, wherein one end of the chain plate is provided with a pin hole, and the other end is fixed with the pivot pin; the pivot pin fixed on each chain plate is inserted into the pin hole of another chain plate, so that the chain plates are pivoted with each other through pivot pins and arranged in two intersecting rows.

9. The endoscopic surgical cutting stapler with a chain articulation as in claim 1, wherein some chain plates are provided with pin holes at both ends, and other chain plates are fixed with pivot pins at both ends, the pivot pin of each chain plate with the pivot pin is inserted into the pin hole of each chain plate with the pin hole, so that the chain plates are pivoted with each other and arranged in two intersecting rows.

10. The endoscopic surgical cutting stapler with a chain articulation as in claim 1, wherein the slide bar is formed by a slide support and a pushing plate linked with each other, and the pushing plate is fabricated by using a thin plate made of a hyperelastic Ti—Ni alloy.

11. The endoscopic surgical cutting stapler with a chain articulation as in claim 1, wherein the operating mechanism drives a proximal end of a first-stage chain plate at the most proximal end of the chain articulation, so that the first-stage chain plate of the chain articulation rotates around the pivot pin, thereby generating a first-stage angle; a second-stage chain plate at the sub-most proximal end is driven by the pivot pin of the first stage-plate and is under mesh transmission of the teeth at the distal end of the extension tube and the teeth of the second-stage chain plate, and the angle of the first-stage chain plate is multiplied and transmitted to an angle of the second-stage chain plate, so that the first-stage angle is multiplied to be a second-stage angle; a third-stage chain plate is driven by the pivot pin of the second-stage chain plate and is under mesh transmission of the teeth of the first-stage chain plate and the teeth of the third-stage chain plate, and the angle of the second-stage chain plate is then multiplied and transmitted to an angle of the third-stage chain plate, so that the second-stage angle is multiplied to be a third-stage angle; a fourth-stage chain plate is driven by the pivot pin of the third-stage chain plate and is under mesh transmission of the teeth of the second-stage chain plate and the teeth of the fourth-stage chain plate, and the angle of the third-stage chain plate is multiplied and transmitted to an angle of the fourth-stage chain plate, so that the third-stage angle is multiplied to be a fourth-stage angle; a fifth-stage chain plate is driven by the pivot pin of the fourth-stage chain plate and is under mesh transmission of the teeth of the third-stage chain plate and the teeth of the fifth-stage chain plate, and the angle of the fourth-stage chain plate is multiplied and transmitted to an angle of the fifth-stage chain plate, so that the fourth-stage angle is multiplied to be a fifth-stage angle; the rest is done in the same manner, until the end effector is driven by the pivot pin of an N-stage chain plate and is under mesh transmission of teeth of a (N−1)-stage chain plate and the teeth of the end effector, and an angle of the N-stage chain plate is multiplied and transmitted to an angle of the end effector, so that the N-stage angle is multiplied to be a (N+1)-stage angle; in this manner, when the operating mechanism controls an action of the chain articulation, transmission of the operating mechanism at the distal end of the extension tube is transformed to be the angle of the first-stage chain plate at the most proximal end of the chain articulation; through mesh transmission of the teeth of adjacent chain plates in the same row, the angle of the first-stage chain plate is multiplied through (N+1) stages and transmitted to the angle of the end effecor.

* * * * *